United States Patent [19]

Smith

[11] Patent Number: 5,098,386
[45] Date of Patent: Mar. 24, 1992

[54] INFANT NASAL SUCTION APPARATUS

[76] Inventor: Ina L. Smith, 2426 Acton St., Berkeley, Calif. 94702-2110

[21] Appl. No.: 701,768

[22] Filed: May 17, 1991

[51] Int. Cl.⁵ .............................................. A61M 1/00
[52] U.S. Cl. ..................................... 604/152; 604/35; 604/54; 604/224
[58] Field of Search ...................... 604/54, 35, 36, 131, 604/133, 135, 146, 151, 152, 212, 214, 319, 224, 143, 144; 128/765, 767

[56] References Cited

U.S. PATENT DOCUMENTS

| | | | |
|---|---|---|---|
| 2,595,493 | 5/1952 | Slaby et al. | 604/214 |
| 4,089,624 | 5/1978 | Nichols et al. | 604/152 |
| 4,578,060 | 3/1986 | Huck et al. | 604/133 |
| 4,643,719 | 2/1987 | Garth et al. | 604/133 |
| 4,790,818 | 12/1988 | De Luca et al. | 604/54 |
| 4,995,386 | 2/1991 | Ng | 604/319 |
| 5,002,534 | 3/1991 | Rosenblatt | 604/133 |
| 5,009,637 | 4/1991 | Newman et al. | 604/143 |

FOREIGN PATENT DOCUMENTS

| | | | |
|---|---|---|---|
| 1409278 | 7/1988 | U.S.S.R. | 604/319 |
| 124637 | 4/1919 | United Kingdom | 604/224 |
| 2140302 | 11/1984 | United Kingdom | 604/224 |

Primary Examiner—Gene Mancene
Assistant Examiner—Michael Lynch
Attorney, Agent, or Firm—Leon Gilden

[57] ABSTRACT

A central housing includes a coaxially reciprocatable screw member operative through a selectively actuated drive motor to effect reciprocation of the screw within the housing. The screw member includes a piston mounted at a forward distal end thereof mounting a flexible bag therewithin, wherein the bag directs suction from a forwardly coaxially mounted nozzle into the bag.

3 Claims, 4 Drawing Sheets

INFANT NASAL SUCTION APPARATUS

BACKGROUND OF THE INVENTION

1. Field of the Invention

The field of invention relates to nasal apparatus, and more particularly pertains to a new and improved infant nasal suction apparatus wherein the same is arranged for extraction of mucus and the like from an infant's nasal passageways.

2. Description of the Prior Art

Infants and small children are subject to nasal infection and blockage. Various mechanical type operative vacuum devices are provided in the prior art. Such a device is exemplified in Anderson U.S. Pat. No. 2,879,768 setting forth the construction of an ear syringe to effect vacuum through a forwardly positioned nozzle utilizing a squeeze-type bulb construction.

Rossi U.S. Pat. No. 4,806,101 sets forth an apparatus utilizing a further example of a squeeze chamber that is manually depressed for creating pneumatic action and suction through a forward nozzle.

Miller U.S. Pat. No. 1,766,668 is a further example of a manually operated syringe bulb construction.

As such, it may be appreciated that there continues to be a need for a new and improved infant nasal suction apparatus as set forth by the instant invention which addresses both the problems of ease of use as well as effectiveness in construction in removing blockage and obstruction from a nasal passage of an infant and in this respect, the present invention substantially fulfills this need.

SUMMARY OF THE INVENTION

In view of the foregoing disadvantages inherent in the known types of nasal canal apparatus now present in the prior art, the present invention provides an infant nasal suction apparatus wherein the same utilizes a drive motor to effect suctioning through a forward nozzle mounted coaxially of a central housing. As such, the general purpose of the present invention, which will be described subsequently in greater detail, is to provide a new and improved infant nasal suction apparatus which has all the advantages of the prior art nasal suction apparatus and none of the disadvantages.

To attain this, the present invention provides a central housing including a coaxially reciprocatable screw member operative through a selectively actuated drive motor to effect reciprocation of the screw within the housing. The screw member includes a piston mounted at a forward distal end thereof mounting a flexible bag therewithin, wherein the bag directs suction from a forwardly coaxially mounted nozzle into the bag.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved infant nasal suction apparatus which has all the advantages of the prior art nasal suction apparatus and none of the disadvantages.

It is another object of the present invention to provide a new and improved infant nasal suction apparatus which may be easily and efficiently manufactured and marketed.

It is a further object of the present invention to provide a new and improved infant nasal suction apparatus which is of a durable and reliable construction.

An even further object of the present invention is to provide a new and improved infant nasal suction apparatus which is susceptible to a low cost of manufacture with regard to both materials and labor, and which accordingly is then susceptible of low prices of sale to the consuming public, thereby making such infant nasal suction apparatus economically available to the buying public.

Still yet another object of the present invention is to provide a new and improved infant nasal suction apparatus which provides in the apparatuses and methods of the prior art some of the advantages thereof, while simultaneously overcoming some of the disadvantages normally associated therewith.

Still another object of the present invention is to provide a new and improved infant nasal suction apparatus wherein the same is arranged for removal of excess fluid and mucus from an infant nasal passageway.

These together with other objects of the invention, along with various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
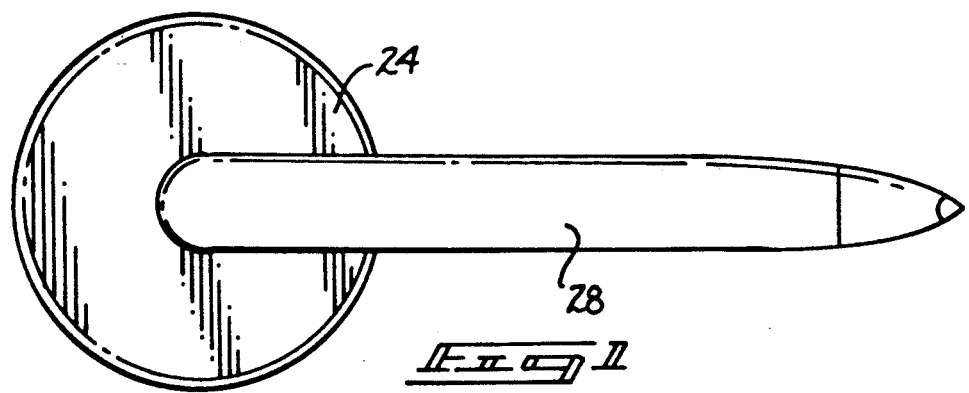
FIG. 1 is an orthographic top view of the instant invention.
Figure 2:
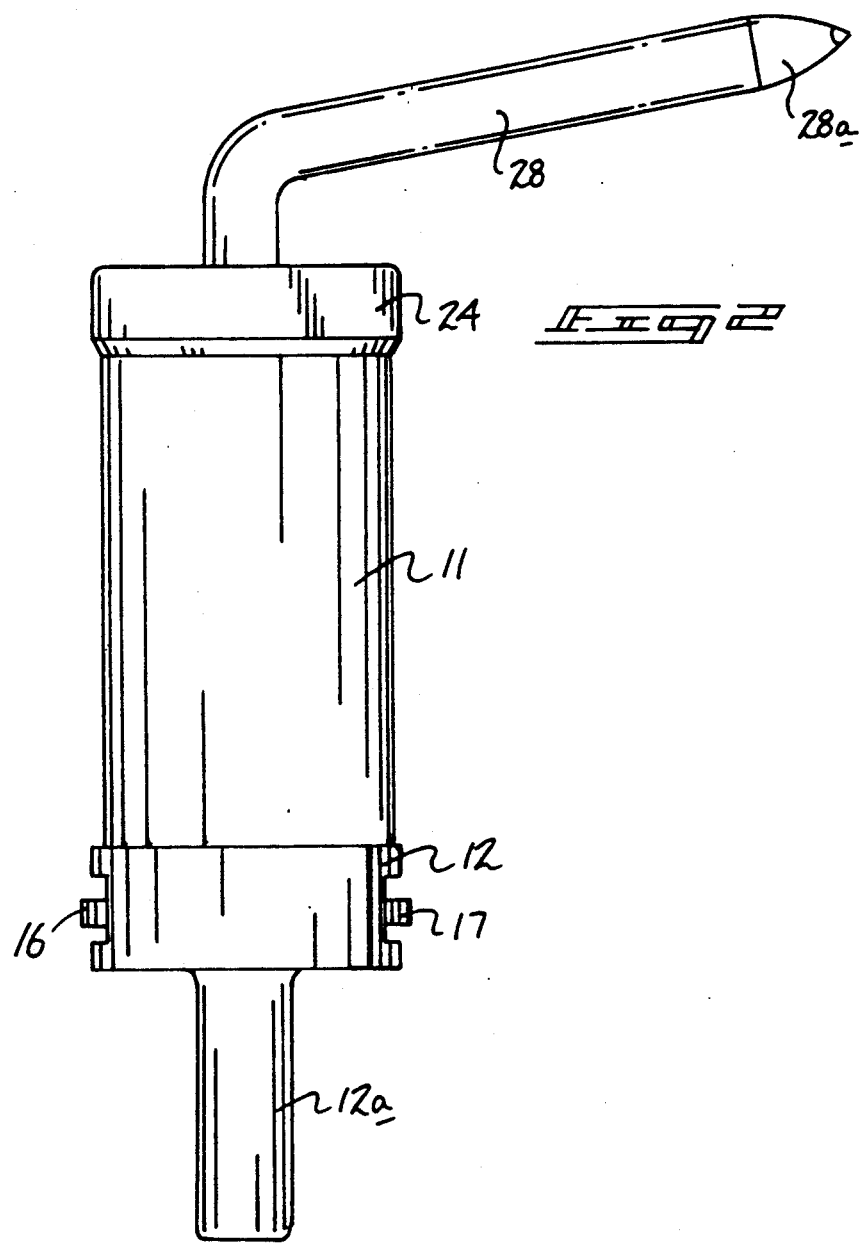
FIG. 2 is an orthographic side view, taken in elevation, of the instant invention.
Figure 3:
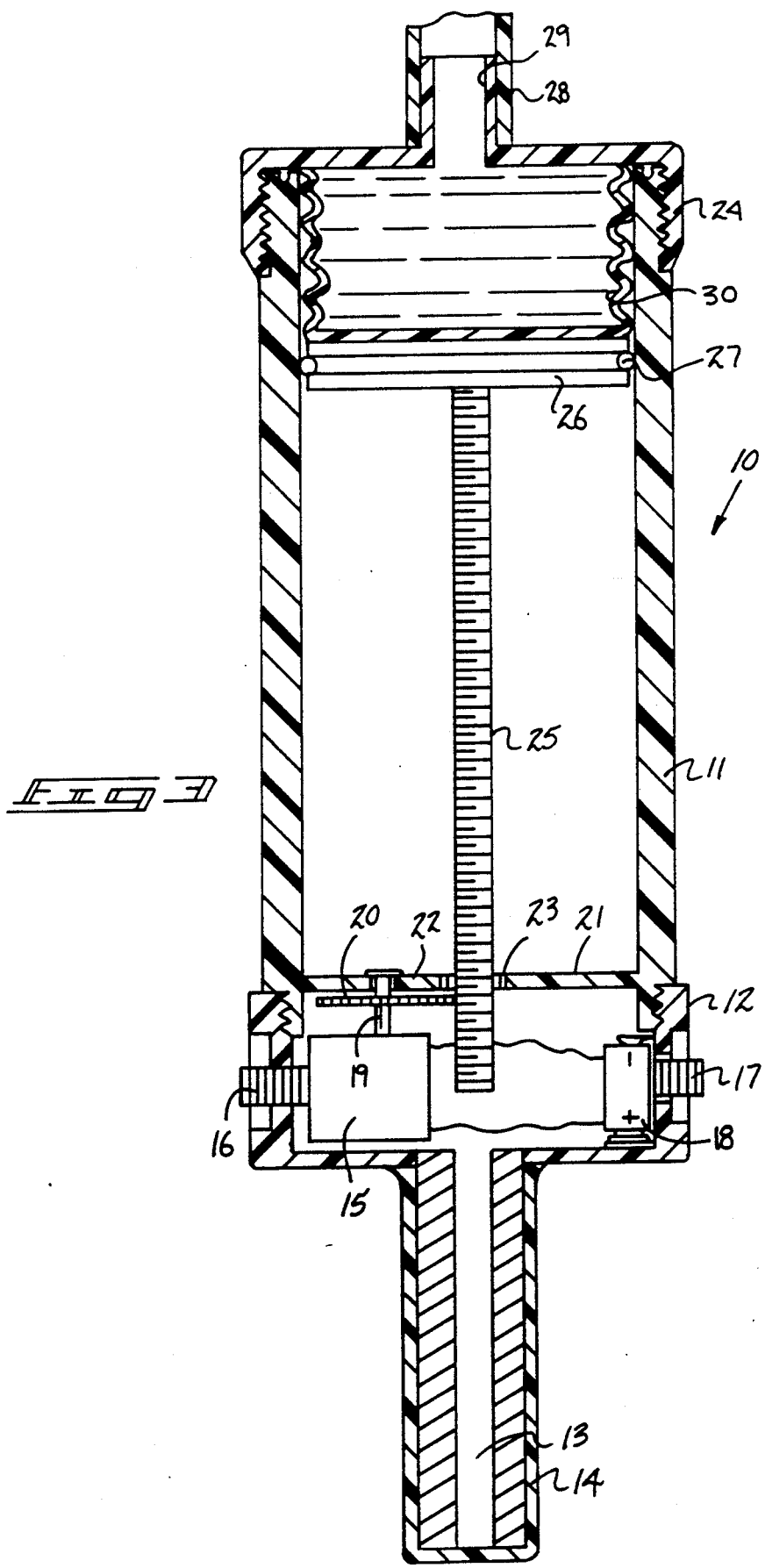
FIG. 3 is an orthographic cross-sectional illustrational of the instant invention.
Figure 4:
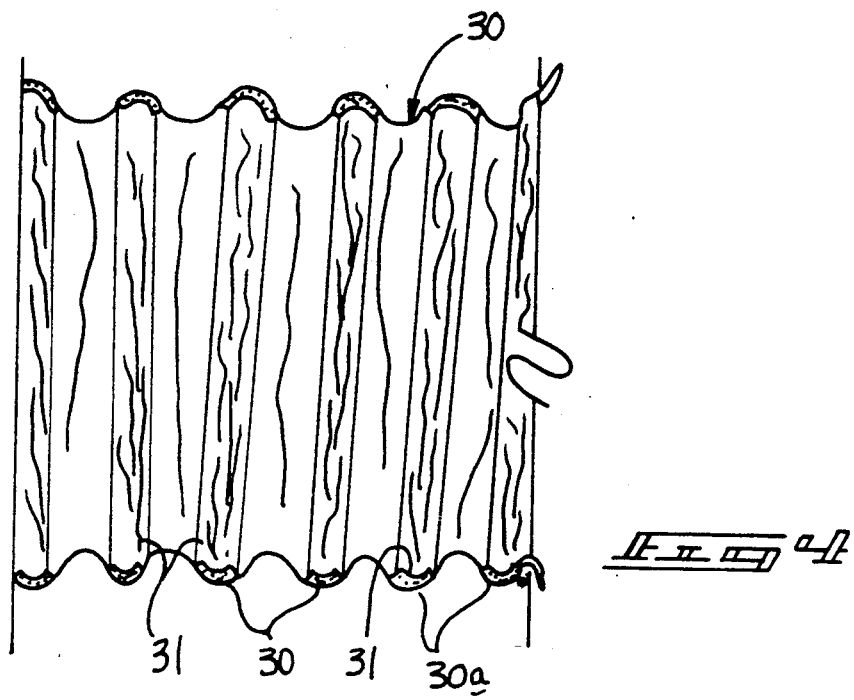
FIG. 4 is an orthographic cross-sectional illustration of the bag construction utilized by the instant invention.

With reference now to the drawings, and in particular to FIGS. 1 to 7 thereof, a new and improved infant nasal suction apparatus embodying the principles and concepts of the present invention and generally designated by the reference numeral 10 will be described.

More specifically, the infant nasal suction apparatus 10 of the instant invention essentially comprises an elongate coaxially aligned cylindrical central housing 11 removably mounting a first end cap 12 at a rear terminal end thereof by intercommunicating threads. A cap cylindrical cavity 13 is coaxially aligned with the housing 11 and the end cap 12 mounted within a cylindrical end cap projection 12a that is also coaxially aligned with the housing 11, wherein the cylindrical cavity 13 is defined by a predetermined diameter substantially equal to the predetermined diameter defined by a gear shaft rod 25, in a manner to be discussed in more detail below. The cylindrical cavity 13 is formed within the lubricant impregnated guide bushing 14, as illustrated.

Figure 5:
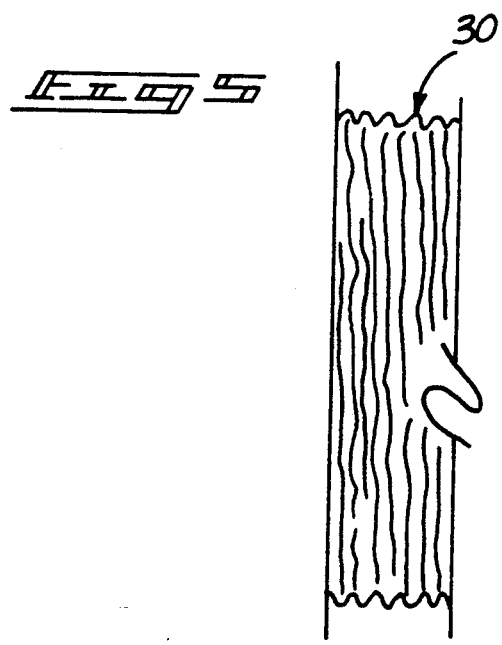
FIG. 5 is an orthographic side view utilized by the invention in a collapsed configuration.

A drive motor 15 mounted within the end cap 12 includes a drive motor reversing switch 16 projecting through a cylindrical skirt of the end cap 12 and is selectively operative through an on/off switch 17, including a battery 18, wherein the on/off switch 17 projects through a diametrically opposed side portion of the first end cap 12. The drive motor 15 includes an output drive shaft 19 mounting a drive shaft gear 20 fixedly thereto, wherein a lower terminal end of the drive shaft 19 is aligned and positioned within a first guide bore 22 formed through a central housing web 21 that is orthogonally and integrally mounted to the interior of the housing 11 relative to an axis defined by the housing 11. The external driven gear shaft rod 25 is coaxially aligned with the housing 11 and cooperates with the drive shaft gear 20 to effect reciprocation of the gear shaft rod 25 relative to the housing 11, wherein the rod 25 is received within the end cap cylindrical cavity 13 when in a retracted position. The gear shaft rod 25 is also positioned and aligned within a second guide bore 23 coaxially directed through the central housing web 21, as illustrated. A suction piston 26 is mounted at a forward distal end of the gear shaft rod 25 mounting a suction piston ring 27 circumferentially thereabout to effect a sealing relationship relative to an interior surface of the cylindrical central housing 11. The housing 11 threadedly mounts a second housing end cap 24 at the forward terminal end thereof remote from the rear terminal end thereof mounting the first end cap 12. The second end cap 24 includes a cap projecting tube 29 coaxially thereof mounting an "L" shaped nozzle 28 thereon, wherein the nozzle 28 is formed with a conical tip 28a to enhance insertion within a nasal cavity or passageway of an infant. A pleated bag member 30 is fixedly mounted to a forward surface of the piston 26, wherein the bag member 30 includes parallel pleats 30a. The pleats 30a have contained therewithin (see FIG. 4) annular bacterial paste rings 31 formed within interior surfaces of each of the pleats. When the pleats are in a folded configuration, as illustrated in FIG. 5, in a first position with the piston in a forward orientation relative to the housing 11, the paste is folded, whereupon extension of the bag member 30 in a second or extended position exposes the bacterial paste to accommodate mucus and the like therewithin to effect sanitizing of fluid directed into the bag member 30.

Figure 6:
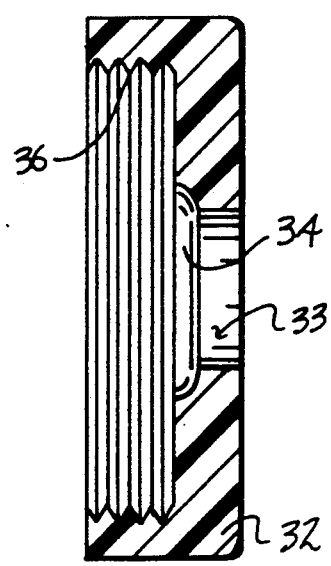
FIG. 6 is an orthographic cross-sectional illustration of a further forward cap member utilized by the invention.
Figure 7:
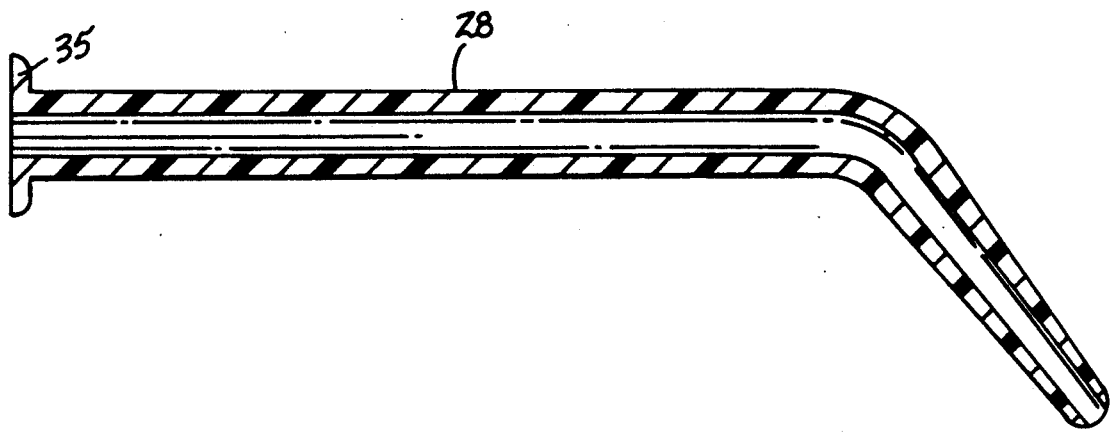
FIG. 7 is an orthographic cross-sectional illustration of a forward nozzle utilized in association with the cap of FIG. 6.

FIG. 6 illustrates a modified second cap 30 that includes a central opening 33 formed with a conical recess 34 projecting into the central opening 33, wherein the conical recess 34 receives in a complementary manner, a conical base 35 of the nozzle 28. The internally threaded skirt 36 of the modified second cap 32 is again secured to the forward terminal end of the housing 11 in a like manner as the second cap 24.

It should be noted that the bag is captured between the forward terminal end of the housing 11 and the end cap 24, as illustrated, to secure the bag relative to the end cap. It should be understood that rearwardly direction of the piston 26 by means of the gear shaft rod 35 being directed rearwardly into the end cap cylindrical cavity 13 that further aligns the rod 25, suction is imparted into the cavity defined between a forward source of the piston 26 and the interior surface of the cap 24 to effect drawing of mucus through the nozzle 28 into the bag 30 where it is acted upon by the bacterial paste rings 31 contained within the pleats 30a.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An infant nasal suction apparatus, comprising:
an elongate cylindrical housing, the cylindrical housing including a housing rear terminal end and a housing forward terminal end, the housing rear terminal end including a first end cap mounted releasably thereto, and the housing forward terminal end including a housing second end cap removably mounted thereto, the central housing including a central housing web, the central housing web fixedly mounted within the housing adjacent the housing rear terminal end, with the central housing including a housing axis, with the housing web oriented orthogonally relative to the housing axis, and a gear shaft rod reciprocatably and coaxially mounted within the central housing, and coaxially directed through the central housing web within a gear shaft rod guide bore coaxially directed through the housing web, and the gear shaft rod including a piston member mounted at a forward terminal end of the gear shaft rod orthogonally oriented relative to the housing axis, and drive means for effecting reciprocation of the gear shaft rod for providing a suction between the piston and the second end cap, the second end cap including a nozzle coaxially mounted thereto for directing fluid through the nozzle into the housing between the second end cap and the piston, and wherein the drive means includes a drive motor fixedly mounted within the first end cap, the drive motor including a reversing switch projecting through a side wall of the first end cap, and the drive means further including an on/off switch mounted within the end cap spaced from the drive motor, and a battery, and the drive motor including an output drive shaft, the output drive shaft rotatably mounted within a drive shaft bore formed within the central housing web, and a drive shaft gear mounted to the drive shaft to effect reciprocation of the gear shaft rod.

2. An apparatus as set forth in claim 1 wherein the first end cap includes a rearwardly projecting cylindrical end cap coaxially aligned with the central housing, and including a guide bushing therewith, the guide bushing including an end cap cylindrical cavity defined by a predetermined diameter, the shaft rod equal to the predetermined diameter complimentarily received within the cylindrical cavity, wherein the cylindrical cavity is coaxially aligned with the central housing.

3. An apparatus as set forth in claim 2 including a pleated bag member mounted between the piston and the second end cap, the bag member including a plurality of annular pleats, and at least one of said annular pleats including an annular bacterial paste ring coated to an interior surface of the at least one of said pleats, and the annular bacterial paste ring covered by at least one of said pleats when in a contracted position when the piston is positioned adjacent the second end cap, and the annular bacterial paste ring exposed when the bag member is an extended position when the piston is positioned in a further position with the gear shaft rod positioned within the end cap cylindrical cavity.

* * * * *